US011331361B2

(12) United States Patent
Lo

(10) Patent No.: US 11,331,361 B2
(45) Date of Patent: May 17, 2022

(54) HYBRID HERBAL AND DRUG COMPOSITION AND METHOD OF FORMULATION

(71) Applicant: Shui Yin Lo, Arcadia, CA (US)

(72) Inventor: Shui Yin Lo, Arcadia, CA (US)

( * ) Notice: Subject to any disclaimer, the term of this patent is extended or adjusted under 35 U.S.C. 154(b) by 94 days.

(21) Appl. No.: 16/858,352

(22) Filed: Apr. 24, 2020

(65) Prior Publication Data

US 2020/0261527 A1    Aug. 20, 2020

Related U.S. Application Data

(63) Continuation of application No. 16/275,778, filed on Feb. 14, 2019, now Pat. No. 10,857,194.

(51) Int. Cl.

| | | |
|---|---|---|
| A61K 36/00 | (2006.01) |
| A61K 36/481 | (2006.01) |
| A61K 35/32 | (2015.01) |
| A61K 33/42 | (2006.01) |
| A61K 31/203 | (2006.01) |
| A61K 36/18 | (2006.01) |
| A61K 36/232 | (2006.01) |
| A61K 31/59 | (2006.01) |
| A61K 31/51 | (2006.01) |
| A61K 31/4418 | (2006.01) |
| A61K 33/22 | (2006.01) |
| A61K 35/64 | (2015.01) |
| A61K 33/30 | (2006.01) |
| A61K 35/644 | (2015.01) |
| A61K 35/586 | (2015.01) |
| A61K 33/06 | (2006.01) |

(52) U.S. Cl.
CPC .......... *A61K 36/481* (2013.01); *A61K 31/203* (2013.01); *A61K 31/4418* (2013.01); *A61K 31/51* (2013.01); *A61K 31/59* (2013.01); *A61K 33/06* (2013.01); *A61K 33/22* (2013.01); *A61K 33/30* (2013.01); *A61K 33/42* (2013.01); *A61K 35/32* (2013.01); *A61K 35/586* (2013.01); *A61K 35/64* (2013.01); *A61K 35/644* (2013.01); *A61K 36/18* (2013.01); *A61K 36/232* (2013.01)

(58) Field of Classification Search
CPC . G16H 20/90; A23V 2300/12; A23C 2240/20
See application file for complete search history.

(56) References Cited

U.S. PATENT DOCUMENTS

| 2013/0022663 A1* | 1/2013 | Buckman | A61K 9/0014 424/450 |
| 2015/0335740 A1* | 11/2015 | Lo | A61K 45/06 514/789 |
| 2016/0000917 A1* | 1/2016 | Farrington | A61K 33/06 424/542 |

* cited by examiner

*Primary Examiner* — Qiuwen Mi
(74) *Attorney, Agent, or Firm* — Elizabeth Yang

(57) ABSTRACT

A hybrid herbal and drug composition includes an amount of Chinese herb about 0.01 to 5% by weight of the composition; an amount of animal-based matter about 0.01 to 5% by weight of the composition; an amount of vitamin about 0.01 to 5% by weight of the composition; an amount of mineral about 0.01 to 5% by weight of the composition; an amount of hormone about 0.01 to 5% by weight of the composition; an amount of factory produced product about 0.01 to 5% by weight of the composition; and an amount of the purified water about 70% to 99.94% by weight of the composition.

1 Claim, 5 Drawing Sheets

| 100 | Herbs in Chinese Medicine | | |
|---|---|---|---|
| | Name | Latin names- Scientific names | Chinese Name |
| | General | | |
| 102 | Renshen | Radix Ginzeng | 人参 |
| 104 | Xiyangshen | Radix Panacis Quinquefolii | 西洋参 |
| 106 | Dongchongxiacao | Cordyceps | 冬虫夏草 |
| 108 | Lingzhi | Ganoderma | 灵芝 |
| | For Cancer | | |
| 110 | Dang Shen | Radix Codonopsis | 党参 |
| 112 | Huangqi | Radix Astragali | 黄芪 |
| 114 | Baizhu | Rhizoma Atractylodis Macrocephalae | 白术 |
| 116 | Xianhecao | Herba Agrimoniae | 仙鹤草 |
| 118 | Buguzhi | Fructus Psoraleae | 补骨脂 |
| 120 | Dang gui | Radix Angelicae Sinensis | 当归 |
| 122 | Renshen | Radix Ginzeng | 人参 |
| 124 | Xiyangshen | Radix Panacis Quinquefolii | 西洋参 |
| 126 | Gouqizi | Fructus Lucii | 枸杞子 |
| 128 | Nuzhenzi | Fructus Ligustri Lucidi | 女贞子 |
| 130 | Fuling | Poria | 茯苓 |
| | Dimentia and Alzheimer's Disease | | |
| 132 | Wuweizi | Fructus Schisandrae | 五味子 |
| 134 | Danggui | Radix Angelicae Sinesis | 当归 |
| 136 | Fuling | Poria | 茯苓 |
| 138 | Shudihuang | Radix Rehmanniae | 熟地黄 |
| 140 | Huangqi | Radix Astragali | 黄芪 |
| 142 | Gouqizi | Fructus Lycii | 枸杞子 |
| 144 | Xuanzhi | Radix Polugalae | 远志 |
| 146 | Gancao | Radix Glycyrrhise | 甘草 |
| 148 | Renshen | Radix Ginseng | 人参 |
| 150 | Suan Zaoren | Semen Ziziphi Spinosae | 酸枣仁 |
| | Diabetes | | |
| 152 | Tian ua fen | Radix Trichosanthis | 天花粉 |
| 154 | Gegan | Radix Puerariae | 葛根 |
| 156 | Huangqi | Radix Astragali | 黄芪 |
| 158 | Fuling | Poria | 茯苓 |
| 160 | Baizhu | Rhizoma Atraetylodis Macrocephalae | 白术 |
| 162 | Xuanshen | Radix Scrophulariae | 玄参 |
| 164 | Huangbo | Cortex Phellodendri | 黄柏 |
| 166 | Shengdi | Radix Rehmanniae | 生地 |
| 168 | Renshen | Radix Gnseng | 人参 |
| 170 | Gouqizi | Fructus Lycii | 枸杞子 |

FIG. 1A

Animal-Based Matter

| 172 | Lurong | Cornu Cervi Pantotrichum | 鹿茸 |
|-----|--------|--------------------------|------|
| 174 | Gui ban | Carapax et Plastrum Testudinis | 龟板 |
| 176 | bei jia | Carapax Trionycis | 鳖甲 |
| 178 | Fengmi | Mel | 蜂蜜 |

FIG. 1B

200  Non-Small Cell Factory Produced Products for Health and Diseases

Diabetes

| | |
|---|---|
| 202 | Metformin |
| 204 | Glucophage |
| 206 | Victoza |
| 208 | Januvia |
| 210 | Amaryl |
| 212 | Actos |
| 214 | Invokana |
| 216 | Levemir |
| 218 | Glucotrol |
| 220 | Lantus |
| 222 | Glimepiride |
| 224 | Byetta |
| 226 | Bydureon |
| 228 | Farxiga |
| 230 | Humalog |

Breast Cancer

| | |
|---|---|
| 232 | trastuzuhamb(Herceptin) |
| 234 | pertuzuhamb(Perjeta) |
| 236 | tamoxifen |
| 238 | palbociclib(Ibrance) |
| 240 | ribociclib(Kisqali) |
| 242 | everolimus(Afinitor) |
| 244 | doxoribicun(Adriamycin) |
| 246 | epirubicdin(Ellence) |
| 248 | paclitaxel(Taxol) |
| 250 | docetaxel(Taxotere) |

Lung Cancer

| | |
|---|---|
| 252 | Abitrexate (Methotrexate) |
| 254 | Abraxane (Paclitaxel Albumin-stabilized Nanoparticle Formulation) |
| 256 | Afatinib (Dimaleate) |
| 258 | Afinitor (Everolimus) |
| 260 | Alecensa (Alectinib) |
| 262 | Alectinib |
| 264 | Alimta (Pemetrexed disodium) |
| 266 | Alunbrig (Brigatinib) |
| 268 | Atezolizumab |
| 270 | Avastin (Bevacizumab) |

FIG. 2

300 Vitamin
- 302 Vitamin A
- 304 Vitamin D
- 306 Vitamin E
- 308 Vitamin K
- 310 Vitamin B complex
- 312 vitamin B1
- 314 vitamin B2
- 316 Vitamin B3
- 318 Vitamin B6
- 320 Vitamin B12
- 322 Vitamin C

FIG. 3

400 Minerals
- 402 Calcium
- 404 Phosphorous
- 406 Magnessium
- 408 Zinc
- 410 Iron
- 412 Copper
- 414 Manganese
- 416 Chromium
- 418 Selenium
- 420 Iodine
- 422 Potassium
- 424 Boron

FIG. 4

HYBRID HERBAL AND DRUG COMPOSITION AND METHOD OF FORMULATION

CROSS-REFERENCE TO RELATED APPLICATIONS

This application is a continuation of application Ser. No. 16/275,778, filed Feb. 14, 2019, which claims the benefit of a U.S. provisional application No. 62/630,746, filed on Feb. 14, 2018 and entitled "Hybrid Herbal and Drug Composition and Method of Formulation". All of the above-referenced applications are hereby incorporated herein by reference in their entirety.

FIELD OF THE DISCLOSURE

The present invention relates generally to a hybrid herbal and drug composition and method of formulation for healing holistically with alternative and science-based drugs. More so, a hybrid herbal and drug composition combines homeopathic remedies, Natural herbs and animal-based matter, and science-based drugs, vitamins, minerals, and hormones; whereby the combined healing components are diluted in an inert gas environment, polarized with an electrical field, and emulsified and dispersed through ultrasonic mixing, and adding a second herbal and drug composition consisting of both natural herbs and animal-based matter and science-based drugs.

BACKGROUND OF THE DISCLOSURE

Generally, the homeopathic remedies are usually taken orally, and the homeopathic ingredient may be taken to strengthen the body's mechanism for regulating blood pressure. Homeopathic ingredients are prepared by repeated dilution with a diluent, such as water or alcohol. The homeopathic remedies provide the advantage that it was invented two hundred years ago and extensively used in Europe and India. Further, the homeopathic remedies are covered by government health insurance in myriad countries. However, it is always not easy to combine a homeopathic ingredient with another ingredient. The procedure to combine the homeopathic ingredient and the other ingredient is complicated and spend a long of time to complete the procedure.

Therefore, there may exist a desire to combine the homeopathic ingredients with another ingredient more efficiently, and further reduce the toxicity for the homeopathic ingredient and the another ingredient.

All referenced patents, applications and literatures are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. The disclosed embodiments may seek to satisfy one or more of the above-mentioned desires. Although the present embodiments may obviate one or more of the above-mentioned desires, it should be understood that some aspects of the embodiments might not necessarily obviate them.

BRIEF SUMMARY OF THE DISCLOSURE

In a general implementation, a hybrid herbal and drug composition includes at least one natural herb, at least one animal-based matter, or both; at least one vitamin; at least one mineral; at least one hormone; at least one factory produced chemicals; and at least one 15 homeopathic substance or a combination thereof.

In another aspect combinable with the general implementation, the natural herbs can be selected from the group consisting of renshen, xiyangshen, dongchongxiacao, lingzhi, dzng Shen, huangqi, baizhu, xianhecao, buguzhi, dang gui, renshen, xiyangshen, gouqizi, nuzhenzi, fuling, wuweizi, danggui, fuling, shudihuang, huangqui, gouqizi, xuanzhi, gancao, 20 renshen, and suan zaoren.

In another aspect combinable with the general implementation, the animal-based matter can be selected from the group consisting of lurong, gul ban, bei jia, and fengmi.

In another aspect combinable with the general implementation, the factory produced chemicals can be selected from the group consisting of metformin, glucophage, victoza, junuvia, amaryl, actos, invokana, levemir, glucotrol, lantus, glimepiride, byetta, bydureon, farxiga, humalog, trastuzuhamb, pertuzuhamb, tamoxifen, palbociclib, ribociclib, everolimus, doxoribicun, epirubicdin, paclitaxel, docetaxel, abitrexate, abraxane, afatinib, afinitor, alecensa, alectinib, alimta, alunbrig, atezolizumab, and avastin.

In another aspect combinable with the general implementation, the vitamin can be selected from the group consisting of vitamin A, vitamin E, vitamin D, vitamin K, vitamin B complexes, vitamin B1, vitamin B2, vitamin B3, vitamin B6, vitamin B12, and vitamin C.

In another aspect combinable with the general implementation, the minerals can be selected from the group consisting of calcium, phosphorous, magnesium, zinc, iron, copper, manganese, chromium, selenium, iodine, potassium, and boron.

Accordingly, the present disclosure is directed to a hybrid herbal and drug composition having the same that substantially obviate one or more problems due to limitations and disadvantages of the related art.

Among the many possible implementations of the present invention is to create a synergetic effect between homeopathic remedies, Natural herbs and animal-based matter, and science-based drugs in a systematic process for holistic healing of eclectic maladies, such as cancer, diabetes, Alzheimer's diseases, and Parkinson's disease.

Another aspect of the embodiment is directed to methods for formulation of a hybrid herbal and drug composition for healing holistically with alternative and science-based drugs, the method includes:

composing a first solution M consisting of at least one of the following: at least one homeopathic substance, at least one natural herb, at least one animal-based matter, at least one vitamin, at least one mineral, at least one hormone, or at least one factory chemical;

dissolving, solution M in purified water;

applying an electrical field to the mixed solution and the purified water to form a solid water particle solution having a large clump of solid water particles;

vibrating, under inert gas, the large clump of solid water particles with an ultrasonic vibration device directly or through a water bath to break the large clump of solid water particles into a small cluster of solid water particles;

resting the small cluster of solid water particles for a predetermined duration to make the small cluster of solid water particles to form a larger clump of solid water particles;

repeating the vibration, under inert gas, of the larger clump of solid water particles until a predetermined concentration of solid water particles forms in the solid water particle solution;

adding a second solution N to the solid water particle solution.

In another aspect combinable with the method for formulation of a hybrid herbal and drug composition, wherein the each of the first solution M and the second solution N comprises an amount of natural herb generally about 0.01% to 5% by weight of the composition; an amount of animal-based matter generally about 0.01% to 5% by weight of the composition; an amount of vitamin generally about 0.01% to 5% by weight of the composition; an amount of mineral generally about 0.01% to 5% by weight of the composition; an amount of hormone generally about 0.01% to 5% by weight of the composition; and an amount of factory produced chemicals generally about 0.01% to 5% by weight of the composition; and an amount of the purified water generally about 70% to 99.94% by weight of the composition.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above and below as acting in certain combinations and even initially claimed as such, one or more features from a claimed 20 combination can in some cases be excised from the combination, and the claimed combination may be directed to a sub combination or variation of a sub combination.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

It should be noted that the drawing figures may be in simplified form and might not be to a precise scale. In reference to the disclosure herein, for purposes of convenience and clarity only, directional terms such as top, bottom, left, right, up, down, over, above, below, beneath, rear, front, distal, and proximal are used with respect to the accompanying drawings. Such directional terms should not be construed to limit the scope of the embodiment in any manner.

FIGS. 1A and 1B references a Table, listing some of the thousands of Natural herbs used in the hybrid herbal and drug composition, in accordance with an embodiment of the present invention;

FIG. 2 references a Table, listing some of the thousands of factory-made drugs used in 15 the hybrid herbal and drug composition, in accordance with an embodiment of the present invention;

FIG. 3 references a Table, listing some of the hundreds of vitamins used in the hybrid herbal and drug composition, in accordance with an embodiment of the present invention;

FIG. 4 references a Table, listing some of the hundreds of minerals used in the hybrid 20 herbal and drug composition, in accordance with an embodiment of the present invention.

DETAILED DESCRIPTION OF THE EMBODIMENTS

Figure 5:
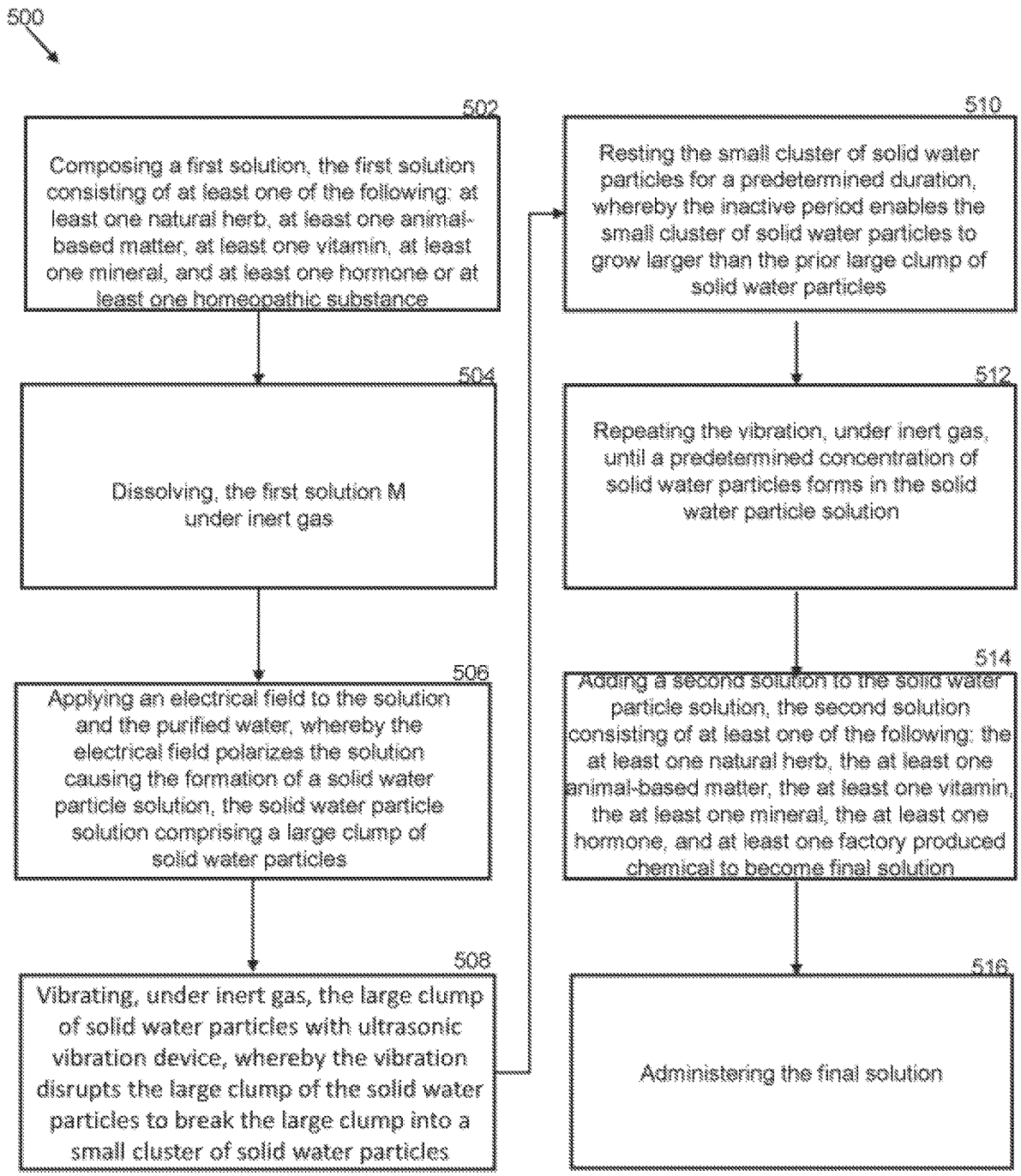
FIG. 5 illustrates a flowchart of an exemplary method of formulation of a hybrid herbal and drug composition for healing holistically with alternative and science-based drugs, m accordance with an embodiment of the present invention.

The different aspects of the various embodiments can now be better understood by turning to the following detailed description of the embodiments, which are presented as illustrated examples of the embodiments defined in the claims. It is expressly understood that the embodiments as defined by the claims may be broader than the illustrated embodiments described below A hybrid herbal and drug composition for the formulation is configured to holistically heal various maladies with a combination of homeopathic remedies, natural grown Natural herb, and science-based drug, vitamin, mineral, and hormones. The hybrid herbal and drug composition, hereafter "composition", combines the efficacy of homeopathic remedies, Natural herbs and animal-based matter, and science-based drugs in a systematic manner to achieve holistic healing of eclectic maladies, such as cancer, diabetes, alzheimer's diseases, and parkinson's disease.

Accordingly, the hybrid herbal and drug composition is formulated through a first solution M which is diluted in an inert gas environment and polarized with an electrical field. Then, the first solution M is emulsified and dispersed through an ultrasonic mixing. Next, a second solution N consisting of natural herbs, animal-based matter, and science-based drugs is added to the first solution M. This systematic formulation process creates a synergy that optimizes the effectiveness of each type of healing ingredient and medicine types.

The hybrid and herbal drug composition is effective in synthesizing elements from each of the three medicine types: the homeopathic remedies, the Natural herb 100 and animal-based matter 172, 174, 176, and 178, and the science-based drug 300. The homeopathic remedies provide the advantage that it was invented two hundred years ago, and extensively used in Europe and India. Further, the homeopathic remedies are covered by government health insurance in myriad countries. Examples include diluting and ultrasonic mixing of homeopathic materials with pure water.

The Natural herb 100 and animal-based matter 172, 174, 176, and 178 provide the advantage that naturally grown parts such as herbs and some parts of animals are grown in nature that share some of the DNA with a human. They are filtered through thousands of years of practice. Only the Natural herb and the animal-based matter 172, 174, 176, and 178 having efficacy are used in the Chinese medicine of the present invention. Examples include Dang Shen for heating cancer, Wuweizi for healing dementia and Alzherimer's disease, and Renshen for general healing.

The science-based drug 300, often used in Western medicines, for treating illness and improving health. The science-based drug 300 are usually obtained from research and high-level scientist, with the backing of billions of dollars. Examples include the vitamin 300 such as Vitamin A and B; and minerals 400 such as Calcium and Phosphorous.

Referring to FIGS. 1-4 of the drawings, the hybrid and herbal drug composition comprises naturally grown herbs 100, animal-based matter 172, 174, 176, and 178; factory produced product 200, vitamin 300, and mineral 400 that are used in formulating the hybrid herbal and drug composition. These ingredients are combined in a sequenced process under typical laboratory procedures known in the art to generate the hybrid and herbal drug composition of the present invention.

In one embodiment, the hybrid herbal and drug composition can be composed with a pure water solution of some material M, wherein the solution M is mixture of three types of chemical substances: homeopathic substances "s"; Natural herb 100 "$h_i$"; and factory produced product 200 $f_j$, including vitamin 300 and mineral 400.

It is known in the art that there are about four hundred common herbs, and over a thousand have been used in Chinese Medicine. Some of the Natural herbs 100 are listed in FIGS. 1A and 1B (Table 1). The present invention utilizes an index system $h_i$, i=100, 102, 104, 106, 108, etc. to indicate a different kind of herbs. The amount in mg/liter of each kind of herbs is given by α.

As shown in FIG. 1A, the Natural herb 100 that is used for treating general maladies comprises Renshen 102, Xiyangshen 104, Dongchongxiacao 106, Lingzhi 108. Natural herbs used for treating cancer include Dzng Shen 110, Huangqi 112, Baizhu 114, Xianhecao 116, Buguzhi 118, Dang gui 120, Renshen 122, Xiyangshen 124, Gouqizi 126, Nuzhenzi 128, Fuling 130. Natural herb which is used for treating dementia and /-\l/heirner's disease comprise Wuweizi 132, Danggui 134, Fuling 136, Shudihuang 138, Huangqui 140, Gouqizi 142, Xuanzhi 144, Gancao 146, Renshen 148, and Suan Zaoren 150.

FIG. 1A further teaches that Natural herb 100 used in the composition for treating diabetes comprises Tian Ua Fen 152, Gegan 154, Huangqi 156, Fuling 158, Baizhu 160, Xuanshen 162, Huangbo 164, Shengdi 166, Renshen 168, and Gouqizi 170.

In another embodiment, as shown in FIG. 1B, the natural animal-based matter 172, 174, 176, and 178 that is also used in the composition to treat maladies, comprises Lurong 172, Gui Ban 174, Bei Jia 176, and Fengmi 178.

According, the amount of Natural herb 100 in the first solution M is generally about 0.01% to 5% by weight of the first solution M. In other words, a total amount of the Natural herb 100 can be generally about 0.1 g to 50 g, and the total amount of the Natural herb 100 can be diluted in one liter of purified water.

In one aspect, the Natural herb 100 in the first solution M can be selected at least one kinds of Natural herb 100 for treating general maladies, cancers, dimentia and Alzheimer's disease, diabetes, and animal-based matters.

Accordingly, each of the amounts for each of the selected Natural herb 100 is the first solution M is approximately 0.1% to 100% by weight of the total amount of the Natural herb 100.

Referring to FIG. 2 of the drawings, the factory produced product 200 which can be used for treating diabetes comprise: Metformin 202, Glucophage 204, Victoza 206, Junuvia 208, Amaryl 210, Actos 212, Invokana 214, Levemir 216, Glucotrol 218, Lantus 220, Glimepiride 222, Byetta 224, Bydureon 226, Farxiga 228, and Humalog 230.

In one embodiment, the factory produced product 200 which can be used for treating breast cancer can be selected from a group consisting of trastuzuhamb 232, pertuzuhamb 234, tamoxifen 236, palbociclib 238, ribociclib 240, everolimus 242, doxoribicun 244, epirubicdin 246, paclitaxel 248, and docetaxel 250.

In another embodiment, the factory produced product 200 can be used for treating lung cancer comprises: Abitrexate 252, Abraxane 254, Afatinib 256, Afinitor 258, Alecensa 260, Alectinib 262, Alimta 264, Alunbrig 266, atezolizumab 268, and Avastin 270

Accordingly, each of the amounts for each of the selected factory produced product 200 is approximately 0.1% to 100% by weight of the total amount of the factory produced product 200 in the first solution M.

Referring to FIG. 3 of the drawings, in yet another embodiment, the factory produced product 200 can be the Vitamin 300, which comprises Vitamin A 302, Vitamin E 304, Vitamin D 306, Vitamin K 308, Vitamin B complexes 310, Vitamin B1 312, Vitamin B2 314, Vitamin B3 316, Vitamin B6 318, Vitamin B12 320, and Vitamin C 322.

Accordingly, each of the amounts for each of the selected vitamin 300 is approximately 0.1% to 100% by weight of the total amount of the vitamin 300 in the first solution M.

Referring to FIG. 4 of the drawings, the mineral 400 used in the manufacture of the composition comprises Calcium 402, Phosphorous 404, Magnesium 406, Zinc 408, Iron 410, Copper 412, Manganese 414, Chromium 416, Selenium 418, Iodine 420, Potassium 422, and Boron 424.

Accordingly, each of the amounts for each of the selected mineral 400 is approximately 0.1% to 100% by weight of the total amount of the mineral 400 in the first solution M.

In one aspect, the amount of factory produced product 200 are given by β in mg/liter. The composition of material M, or the first solution, is given by the following equation, where first solution $M=\Sigma \alpha_i(h_i)+\beta_j(f_j)$, sum over the index one set of i and j. Further, the first solution M is diluted in a large amount of purified water, such as 1 liter.

In the above-mentioned aspect, the present invention utilizes an index system $h_i$, i=100, 102, 104, 106, 108, 110, 112, 114, 116, 118 . . . 178, as shown in FIGS. 1A and 1B, to indicate a different kind of Natural herbs. The amount in mg/liter of each kind of Natural herbs is given by α. The index system $f_j$ of the first solution M, j=202, 204, 206, 208, . . . 270, as shown in FIG. 2, or "j" may be 302, 304, 306, 308 . . . 322, as shown in FIG. 3, or "j" can be 402, 404, 406, 408 . . . 424, as shown in FIG. 4, wherein the amount in mg/liter of each kind of factory produced products is given by β.

In one aspect, $\beta_j (f_j)$ of first solution M can comprise the factory produced product 200 selectively being combined with both of the vitamin 300 and the minerals 400 or be combined with either the vitamin 300 or the minerals 400.

In another aspect, $\beta_j (f_j)$ of first solution M can comprise only the factory produced products 200, wherein a total amount of the factory produced products 200 can be generally about 0.1 g to 50 g. In other words, the amount of factory produced products 200 is generally about to 0.01% to 5% by weight of the first solution M.

In yet another aspect, $\beta_j (f_j)$ of first solution M can comprise only the vitamin 300 wherein the total amount of vitamin 300 in the first solution M is generally about 0.1 g to 50 g. In other words, the amount of vitamin 300 is generally about 0.01% to 5% by weight of the first solution M.

In still yet another aspect, $\beta_j$ ($f_j$) of first solution M can comprise only the minerals 400, wherein the total amount of mineral 400 in the first solution M is generally about 0.1 g to 50 g. In other words, the amount of the minerals 400 is about 0.01% to 5% by weight of the first solution M.

For example, one: First solution M can be composed of the Natural herb 100 only, and, a value of $\beta_j$ ($f_j$) in the first solution M is zero. In one non-limiting embodiment, the first solution M can be composed of three kinds of Natural herbs 100: Huangqi 112, Wuweizi 132, and Danggui 134, wherein the amount of the Huangqi 112 is 1 mg, and the amount of Wuweizi is 1 mg, and the amount of the Danggui is 1 mg, so the total amount of Natural herbs 100 in the first solution M is 3 mg. Further, the total amount of Natural herbs 100 can be diluted in one liter of purified water.

For example two, the first solution M can be composed of only vitamin D 304. In other words, the amount of vitamin D 304 is 0.01% to 5% by weight of the first solution M.

For example, three, the first solution M can be composed of only the minerals 400, such as Magnesium 406. In other words, the amount of the Magnesium 406 is 0.01% to 5% by weight of the first solution M Accordingly, an amount of each of the Natural herbs in the Natural herbs 100 of the first solution M is about 0.1% to 100%. That is to say, there are several Natural herbs 100 which can be selected to compose the total amount of the Natural herbs.

In one aspect, an amount of the first Natural herb inside the Natural herb 100 of the first solution is 5%, and an amount of the second Natural herb inside the Natural herb 100 of the first solution is 30% and an amount of the rest Natural herb inside the Natural herb 100 of the first solution is 65%.

An electrical field is applied to the first solution M and the purified water. The electrical field serves to polarize the mixed solution (the first solution M and the purified water), which causes the formation of a solid water particle solution, including a large clump of solid water particles. The first solution is then shaken under the ultrasound and diluted under inert gas to break down the large clump of solid water particles into a small cluster of solid water particles.

In one embodiment, a vibrating ultrasound device, known in the art may be used to vibrate the first solution M. The inert gas may include gas which does not undergo chemical reactions under a set of given conditions, wherein the inert gas can be purified argon and nitrogen gases.

After the first solution M is then shaken under the ultrasound, and diluted under an inert gas, the first solution M can be placed in a room temperature for a predetermined period to enables the small cluster of solid water particles to become a larger clump of solid water particles which is larger than the prior large clump of solid water particles. And then, the first solution M is then diluted, and shaken again. The above-mentioned dilution process can be repeated numerous times.

The hybrid herbal and drug composition further comprises a second solution N, wherein the second solution N can comprise naturally the Natural herbs 100, shown in FIGS. 1A and 1B, factory produced products 200, in FIG. 2, the vitamin 300, as shown in FIG. 3, and mineral 400, as shown in FIG. 4. The second solution N is given by the following equation: $N=\Sigma\gamma_k(h_k)+\delta_l(f_l)$, sum over sets of index k and l.

In one embodiment, The index system $\delta_l(f_l)$ of the second solution N can be the factory produced product 200, shown in FIG. 2, the vitamin 300, as shown in FIG. 3, and mineral 400, as shown in FIG. 4., wherein l=202, 204, 206, 208, . . . 270, as shown in FIG. 2, or "l" may be 302, 304, 306, 308 . . . 322, as shown in FIG. 3, or "l" can be 402, 404, 406, 408 . . . 424, as shown in FIG. 4, wherein the amount in mg/liter of each kind of factory produced products is given by $\delta_l$. The index system $\gamma_k(h_k)$ of the second solution N can be the Natural herbs 100, wherein k=100, 102, 104, 106, 108, 110, 112, 114, 116, 118 . . . 178, as shown in FIGS. 1A and 1B, to indicate a different kind of herbs. The amount in mg/liter of each kind of herbs is given by $\gamma_k$.

In one aspect, the index system $\delta_l(f_l)$ of second solution N can comprise the factory produced products 200 selectively being combined with both of the vitamin 300 and the minerals 400, or being combined with either the vitamin 300 or the mineral 400 wherein a total amount of the factory produced product 200, the vitamin 300, and the mineral 400 can be diluted in one liter of purified water. Accordingly, each of the amount of the factory produced product 200, the vitamin 300, and the mineral 400 in the second solution N is about 0.1% to 100%. In one embodiment, the amount of the factory produced product 200 is 5% by weight of the total amount of the factory produced product 200, the vitamin 300, and the mineral 400, and the amount of the vitamin 300 is 30% by weight of the total amount of the factory produced product 200, the vitamin 300, and the mineral 400, and the amount of the mineral 400 is 65% by weight of the total amount of the factory produced product 200, the vitamin and the mineral 400.

In another aspect, the index system $\delta_l(f_l)$ of second solution N can comprise only the factory produced products 200, wherein the amount of the factory produced products 200 is generally about 0.1 g to 50 g, and the amount of the factory produced products 200 is diluted with one liter of purified water. In other words, the amount of the factory produced products 200 is generally about 0.01% to 5% by weight of the second solution N.

Accordingly, each of the amounts of each of the factory produced product 200 in the second solution N selected from the group of the factory produced product 200 is 0.1% to 100%. In other words, the factory produced product 200 in the second solution N comprises metformin 202, trastuzumab 232, and abitrexate 252, wherein an amount of the metformin 202 is 5% by weight of the total amount of the factory produced product 200, and an amount of the trastuzumab 232 is 30% by weight of the total amount of the factory produced product 200, and an amount of the abitrexate 252 is 65% by weight of the total amount of the factory produced product 200

In yet another aspect, the index system $\delta_l(f_l)$ of the second solution N can comprises only the vitamin 300, wherein the amount of the vitamin 300 is generally about 0.1 g to 50 g, and the amount of the vitamin 300 is diluted with one liter of purified water. In other words, the amount of vitamin 300 is generally about to 0.01% to 5% by weight of the second solution N.

Accordingly, each of the amounts of each of the vitamin 300 in the second solution N selected from the group of the Vitamin 300 is to 0.1% to 100%. In other words, the Vitamin 300 comprises vitamin A 302, vitamin B1 312, and vitamin B3 316, wherein an amount of the vitamin A 302 is 5% by weight of the total amount of the vitamin 300, and an amount of the vitamin B1 312 is 30% by weight of the total amount of the vitamin 300, and an amount of the vitamin B3 is 65% by weight of the total amount of the vitamin 300.

In still yet another aspect, the index system $\delta_i(f_i)$ of second solution N can comprise only the mineral 400, wherein the amount of the mineral 400 is generally about 0.1 g to 50 g, and the amount of the mineral 400 is diluted with one liter of purified water. In other words, the amount of the mineral 400 is generally about 0.01% to 5% by weight of the second solution N.

Accordingly, each of the amounts of each of the mineral 400 in the second solution N selected from the group of the mineral is 0.1% to 100%. In other words, the mineral 400 comprises Calcium 402, phosphorous 404, and boron 424, wherein an amount of the Calcium 402 is 5% by weight of the total amount of the mineral 400, and an amount of the phosphorous 404 is 30% by weight of the total amount of the mineral 400, and an amount of the boron 424 is 65% by weight of the total amount of the mineral 400.

Accordingly, an amount of each of the Natural herbs in the Natural herbs 100 of the second solution N is about 0.1% to 100%. That is to say, there are several Natural herbs 100 which can be selected to compose the total amount of the Natural herbs.

In one aspect, an amount of the first Natural herb inside the Natural herb 100 of the second solution is 5%, and an amount of the second Natural herb inside the Natural herb 100 of the second solution is 30%, and an amount of the rest Natural herb inside the Natural herb 100 of the second solution is 65%.

For example, four: The second solution N may be composed of the Natural herbs 100 only. All $\delta_j$ may have a value of zero, wherein the second solution N can be composed of Renshen 102 only. The amount of the Renshen 102 is 0.01% to 5% by weight of the second solution N.

In another embodiment, the second solution N can be composed of dongchongxiacao 106 only.

In yet another embodiment, the second solution N can be composed of two, three, or four kinds of Natural herbs 100.

In still yet another embodiment, the second solution N can be composed of factory produced product 200 only.

Additionally, all $\gamma_i$ may have a value of zero, wherein the second solution N may be composed of vitamin 300 only. The amount of the vitamin 300 is 0.01% to 5% by weight of the second solution N.

In one embodiment, the second solution N can be composed of mineral 400 only, wherein the amount of the mineral 400 is 0.01% to 5% by weight of the second solution N. Accordingly, the mineral 400 can comprise Zinc 408 and Calcium 402.

In another embodiment, the second solution N can be composed of Hormone only.

It is also significant to note that the amount of each ingredient or material in the second solution N is administered in smaller dosages. In one embodiment, the dosage of the second solution N is a hundred to a thousand times smaller, than normal daily dosage requirement. These small amounts after being taken in human are carried to the parts of the body that require it by the action of solid water particles produced by the homeopathic procedure.

Accordingly, the second solution N can be mixed with a diluted first solution O from multiple shaken and dilution as described above. It is also significant that the concentration of the second solution N is in general measured in gm/liter (gram per liter), at least one thousand times more than first solution M FIG. 5 illustrates a flowchart of an exemplary method 500 for the formulation of a hybrid herbal and drug composition for healing holistically with alternative and science-based drugs. The method 500 may include an initial Step 502 of composing a first solution M, the first solution M consisting of at least one of the following elements: at least one natural herb 100, at least one animal-based matter 172, 174, 176, and 178, at least one vitamin 300, at least one mineral 400, and at least one hormone.

The method 500 may further comprise a Step 504 of dissolving, under inert gas, the natural herb 100, the animal-based matter 172, 174, 176, and 178, the vitamin 300, the minerals 400, and the hormone in purified water. A Step 506 includes applying an electrical field to the first solution and the purified water to form a mixed solution, wherein the electrical field can polarize the mixed solution and cause the formation of a solid water particle solution, wherein the solid water particle solution comprises a large clump of solid water particles.

In some embodiments, a Step 508 comprises that vibrating, under inert gas, the large clump of solid water particles with an ultrasonic vibration device directly or through a water bath to break down the large clump into a small cluster of solid water particles. A Step 510 comprises that placing the small cluster of solid water particles for a predetermined duration to enables the small cluster of solid water particles to become a larger clump of solid water particles, wherein the particles in the larger clump of solid water particles are larger than the particles in the prior large clump of solid water particles.

In some embodiments, a Step 512 may comprise repeating the vibration, under inert gas, for the larger clump of solid water particles to form a smaller solid water particles solution.

In one aspect in step 512, an amount of each of the Natural herbs 100, the animal-based matter 172, 174, 176, and 178, the vitamin 300, the minerals 400, and the factory produced products 200 is 0.01% to 5% by weight of the smaller solide water particles solution.

A Step 514 comprises adding a second solution to the smaller solid water particles solution, wherein the second solution can be consisted of at least one of the followings: at least one natural herb, the at least one animal-based matter, the at least one vitamin, the at least one mineral, or the at least one hormone. A final Step 516 includes administering the mixture solution of the first solution (smaller solid water particles solution) and the second solution.

Although the process-flow diagrams show a specific order of executing the process steps, the order of executing the steps may be changed relative to the order shown in certain embodiments. Also, two or more blocks shown in succession may be executed concurrently or with partial concurrence in some embodiments. Certain steps may also be omitted from the process flow diagrams for the sake of brevity. In some embodiments, some or all the process steps shown in the process flow diagrams can be combined into a single process.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

Many alterations and modifications may be made by those having ordinary skill in the art without departing from the spirit and scope of the disclosed embodiments. Therefore, it must be understood that the illustrated embodiments have been set forth only for the purposes of example and that it should not be taken as limiting the embodiments as defined by the following claims. For example, notwithstanding the fact that the elements of a claim are set forth below in a certain combination, it must be expressly understood that the embodiment includes other combinations of fewer, more or different elements, which are disclosed herein even when not initially claimed in such combinations.

Thus, specific embodiments and applications of hybrid Herbal and Drug Composition and Method of Formulation have been disclosed. It should be apparent, however, to those skilled in the art that many more modifications besides those already described are possible without departing from the disclosed concepts herein. The disclosed embodiments, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a nonexclusive manner, indicating that the referenced elements, components, or steps may be present, or utilized, or combined with other elements, components, or steps that are not expressly referenced. Insubstantial changes from the claimed subject matter as viewed by a person with ordinary skill in the art, now or later devised, are expressly contemplated as being equivalent within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the embodiments. In addition, where the specification and claims refer to at least one of something selected from the group consisting of A, B, C . . . and N, the text should be interpreted as requiring at least one element from the group which includes N, not A plus N, or B plus N, etc.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims therefore include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

What is claimed:

1. A method for formulation of a hybrid herbal and drug composition for healing holistically with alternative and science-based drugs, the method comprising:
   composing a first solution M consisting of one homeopathic substance,
   dissolving, solution M in purified water to form a mixed solution;
   applying an electrical field to the mixed solution to form a solid water particle solution having a large clump of solid water particles;
   vibrating, under inert gas, the large clump of solid water particles with an ultrasonic vibration device directly or through a water bath to break the large clump of solid water particles into a small cluster of solid water particles;
   resting the small cluster of solid water particles for a predetermined duration to make the small cluster of solid water particles to form a larger clump of solid water particles;
   repeating the vibration, under inert gas, of the larger clump of solid water particles until a predetermined concentration of solid water particles forms in the solid water particle solution;
   adding a second solution N to the solid water particle solution;
   wherein the second solution N comprises an amount of Chinese herb about 0.01 to 5% by weight of the composition; an amount of animal-based matter about 0.01 to 5% by weight of the composition; an amount of vitamin about 0.01 to 5% by weight of the composition; an amount of mineral about 0.01 to 5% by weight of the composition; an amount of hormone about 0.01 to 5% by weight of the composition; and an amount of factory produced product about 0.01% to 5% by weight of the composition; and an amount of the purified water generally about 70% to 99.94% by weight of the composition;
   wherein the at least one Chinese herb from a group consisting of renshen, xiyangshen, dongchongxiacao, lingzhi, dang shen, huangqi, baizhu, xianhecao, buguzhi, dang gui, renshen, xiyangshen, gouqizi, nuzhenzi, wuweizi, danggui, fuling, shudihuang, huangqi, gouqizi, xuanzhi, gancao, renshen, and suan zaoren;
   wherein the at least one animal-based matter from the group consisting of lurong, gui ban, biejia, and fengmi;
   wherein the at least one vitamin from the group consisting of vitamin A, vitamin E, vitamin D, vitamin K, vitamin B complexes, vitamin B1, vitamin B2, vitamin B3, vitamin B6, vitamin B12, and vitamin C;
   wherein the at least one mineral from the group consisting of calcium, phosphorous, magnesium, zinc, iron, copper, manganese, chromium, selenium, iodine, potassium, and boron;
   wherein the at least one factory produced products from the group consisting of metformin, glimepiride, trastuzumab, pertuzumab, tamoxifen, palbociclib, ribociclib, everolimus, doxoribicun, epirubicdin, paclitaxel, docetaxel, abitrexate, afatinib, alectinib, and atezolizumab.

* * * * *